(12) United States Patent
Rojer Ruiz

(10) Patent No.: US 11,610,673 B1
(45) Date of Patent: Mar. 21, 2023

(54) ROJER GATHERING BIOLOGICAL INDEX (ROGBIX) SYSTEM AND CYBERGATH DEVICE

(71) Applicant: Raul Esteban Rojer Ruiz, San Francisco (PA)

(72) Inventor: Raul Esteban Rojer Ruiz, San Francisco (PA)

( * ) Notice: Subject to any disclaimer, the term of this patent is extended or adjusted under 35 U.S.C. 154(b) by 51 days.

(21) Appl. No.: 17/648,906

(22) Filed: Jan. 25, 2022

(51) Int. Cl.
*G16H 40/63* (2018.01)
*G06K 7/14* (2006.01)
*G06F 8/61* (2018.01)

(52) U.S. Cl.
CPC .............. *G16H 40/63* (2018.01); *G06F 8/61* (2013.01); *G06K 7/1417* (2013.01)

(58) Field of Classification Search
CPC ......... G16H 40/63; G06F 8/61; G06K 7/1417
See application file for complete search history.

(56) References Cited

U.S. PATENT DOCUMENTS

| | | |
|---|---|---|
| 10,991,190 B1 | 4/2021 | Luthra et al. |
| 11,030,708 B2 | 6/2021 | Akutagawa et al. |
| 2020/0279339 A1 | 9/2020 | Akutagawa et al. |
| 2020/0367040 A1 | 11/2020 | Richardson et al. |

FOREIGN PATENT DOCUMENTS

WO    WO-2010015843 A1 *  2/2010  ....... G01N 33/54366

\* cited by examiner

*Primary Examiner* — Matthew Mikels
(74) *Attorney, Agent, or Firm* — Carson Patents®

(57) ABSTRACT

The Rojer Gathering Biological Index (ROGBIX) System and CyberGath Device is a system and test kit combination that allows users an easy and convenient way to keep their current tested state of a disease condition such as Covid updated under their own control. It is a system and test kit combination that allows users an easy and convenient automated means to share a positive or negative test result of a tested disease condition that allows users to keep their disease condition test state current and automatically sharable with other users.

13 Claims, 7 Drawing Sheets

FIG. 7

Rogbix Cybergath Indicator Status Table

| Variable | State | Sub-State | SS-State | Status Indicator | Countdown Time |
|---|---|---|---|---|---|
| Tested | | | | | |
| | No | | | No Light | |
| | Yes | Positive | | No Light | |
| | Yes | Negative | | Constant Green Light | 5 Days |
| Vaccinated | | | | | |
| | No | | | No Light | |
| | Yes | Single Dose Version | One Shot | Constant Blue Light | 2 Months |
| | Yes | | Booster | Constant Blue Light | 6 Months |
| | Yes | Two Dose Version | One Shot | Constant Blue Light | 1 Month |
| | Yes | | Two Shots | Constant Blue Light | 6 Months |
| | Yes | | Booster | Constant Blue Light | 6 Months |
| Tested Negative & Vaccinated | | | | Alternating Green Light and Blue Light | |
| Tested Positive & Vaccinated | | | | No Light | |

ROJER GATHERING BIOLOGICAL INDEX (ROGBIX) SYSTEM AND CYBERGATH DEVICE

TECHNICAL FIELD OF THE INVENTION

This invention relates generally to a Rojer Gathering Biological Index (ROGBIX) System and CyberGath Device system, in the form of a software application and a disease condition test kit, for the purpose of allowing the user to inter-communicate with other users their disease condition negative status by vibration or visible light emission.

BACKGROUND

There are systems and devices available today that enable users to communicate their disease condition test states. Social media and networking applications would allow a user to enter their own data and share their disease condition test state with other users, who then choose to view the posts from said user. Some medical test labs offer sharing of test results to social media as well.

There are systems and test kits to detect positive and negative presence of disease states to include Covid. These systems and test kits really only report a result which must then be actively shared by a user wishing to share the result.

There is not an automated system under a user's control with automation to enable a user to get reminders and/or notices to get a new test to after the time of utility of the prior test has expired.

What is not present in the prior art is a system and test kit combination that allows users an easy and convenient way to keep their current tested state updated under their own control. Further lacking in the prior art is a system and test kit combination that allows users an easy and convenient automated means to share a current disease condition tested state (positive or negative for the disease condition). In light of the foregoing prior art, there is a need for a system and test kit combination to better allow users to keep their disease condition test state current and automatically shareable with other users, such as the invention documented herein.

BRIEF SUMMARY OF THE INVENTION

According to a first aspect of the invention there is a Rojer Gathering Biological Index (ROGBIX) System, CyberGath, comprising a method for a user to self-identify a tested condition status and to actively communicate said tested condition status to a second user; comprising installing an application on a first smart device having a screen; registering said user; acquiring a test data for a condition, if available, from an authorized test data reporter; conducting a test on said user for said condition; comprising scanning a visual code; verifying said visual code; collecting a bodily fluid sample from said user; testing said bodily fluid; verifying test results; generating a new test result having a positive or negative result for a condition and creating a notice in a window on said smart device; comprising a first visible solid color panel display (VSCPD) covering more than fifty percent of said screen when said new test result is negative for a tested condition and no VSCPD when said new test result is positive. Further features of the invention are disclosed in dependent claims connected to the first aspect.

According to a second aspect of the invention there is a Rojer Gathering Biological Index (ROGBIX) System, CyberGath, comprising a method for a user to self-identify a tested covid condition status and to actively communicate notice of said tested condition status to a second user using this method, comprising installing an application on a smartphone connected to a smart device having a screen; registering said user; acquiring a test data for said tested covid condition from an authorized test data reporter; conducting a test on said user for said condition; comprising scanning a visual code; verifying said visual code; collecting a saliva sample from said user; testing said saliva; verifying said test and producing a results code; generating a test result having a positive or negative result for said tested covid condition and creating a notice in a window on said smart device, comprising a visible solid color panel display (VSCPD) covering more than fifty percent of said screen when said test result is negative for a tested covid condition and no VSCPD when said test result is positive. Further features of the invention are disclosed in dependent claims connected to the second aspect.

An advantage of the Rojer Gathering Biological Index (ROGBIX) System is that it is a system and test kit combination that allows users an easy and convenient way to keep their current tested state updated under their own control. Further, the present invention is a system and test kit combination that allows users an easy and convenient automated means to share a positive or negative test result of a tested disease condition. The Rojer Gathering Biological Index (ROGBIX) System is a system and test kit combination that allows users to keep their disease condition test state current and automatically sharable with other users.

The invention will now be described, by way of example only, with reference to the accompanying drawings in which:

BRIEF DESCRIPTION OF THE DRAWINGS

FIG. 7 is a table showing the status indicator colors and countdown time to expiration of a test result or vaccine date used according to the invention.

DETAILED DESCRIPTION

Figure 1:
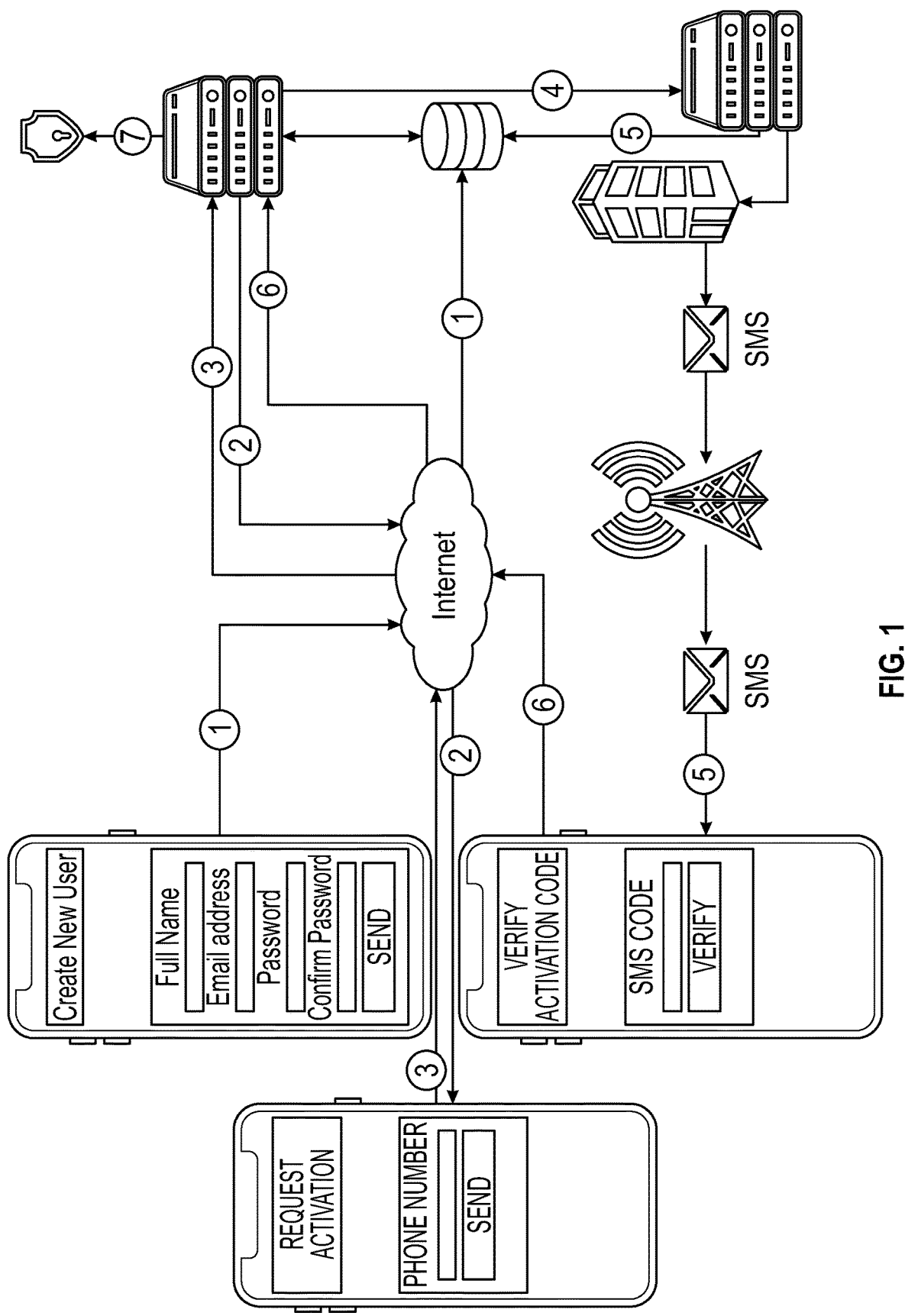
FIG. 1 is a flow diagram view of the interconnections used by the application database according to the invention.

The detailed embodiments of the present invention are disclosed herein. The disclosed embodiments are merely exemplary of the invention, which may be embodied in various forms. The details disclosed herein are not to be interpreted as limiting, but merely as the basis for the claims and as a basis for teaching one skilled in the art of how to make and use the invention.

References in the specification to "one embodiment," "an embodiment," "an example embodiment," etcetera, indicate that the embodiment described may include a particular feature, structure, or characteristic but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

According to the present invention, the ROGBIX gathering biological index system is an auto-identifier device which allows a user to inter-communicate with other users their equal Covid Negative condition by vibration or visible light emission.

The present invention is a technologic invention that functions by joining several machines, devices, methods, and processes, that together can carry out a function different from the individual functions of each one of the above when they are not working jointly.

The set of technologies with the application, processes, and logarithms innovated by the ROGBIX gathering biological index system results in a new technology that can be used to resolve a problem that the above mentioned technological components by themselves cannot resolve. It is the conjunction of these components, as used within the ROGBIX gathering biological index system, that results if the present new application, processes, and innovations have a different function and can indeed resolve the problem of the prior art lacking a system and test kit combination that allows users to keep their disease condition test state current and automatically sharable with other users.

The invention is useful to eliminate the indiscriminate and widespread social distancing of the human population to avoid the Covid-19 contagion when people are in close proximity. The invention is also useful to resolve several simultaneous mutual identification problems such as dispatch condition test state, vaccine administration, vaccine booster administration, and the expirations after a certain time, like those shown in FIG. 7.

Up until now there is not a technological tool, device, or method that can identify and differentiate, in real time, which individuals do not have covid 19; and at the same time notify such condition one to another in an automated fashion. The present invention provides the advantages and goes further, basing the disease condition test state on a saliva based Covid test to show and keep current a negative result of a Covid test.

It is the lack of this technological tool, which can simultaneously detect who is Covid-positive and who is Covid-negative in a group of people who converge, why social distancing is being used to mitigate the possible transmission of Covid-19 among people. More specifically, when the difference can't be established in social groups, nor can there be a distinction between healthy individuals from those individuals that are infected and afflicted with Covid the obvious option has been to maintain a social distancing across the board. The result is that healthy people who are not infected can not meet with their non-infected peers without the mandated distancing. The distancing among individuals has curtailed social interaction worldwide affecting human mobility (freedom of movement) and the effect has trickled down to all social, economic, cultural, religious, business, educational, and recreative activities of the entire world population.

To resolve the generalized social distancing problem the present invention can instantly identify those individuals who have a Covid-Negative status so they could get together safely. The system and test kit combination of the present invention resolves the great global distancing problem and its adverse effects, making social gathering possible among individuals who know each other, as well as total strangers, using the internet connected cyber technology of the present invention.

The present invention consists of software application elements of existing technology, combining them as a whole, together with new formulated algorithms and new processes designed by the present inventor, which allows individuals with the same Covid Negative Status to automatically identify each other in real time. Once people (a plurality of users) can automatically share the information that they are not contagious among each other, as provided by the present invention, they can meet and interact normally and without social distancing.

Figure 4:
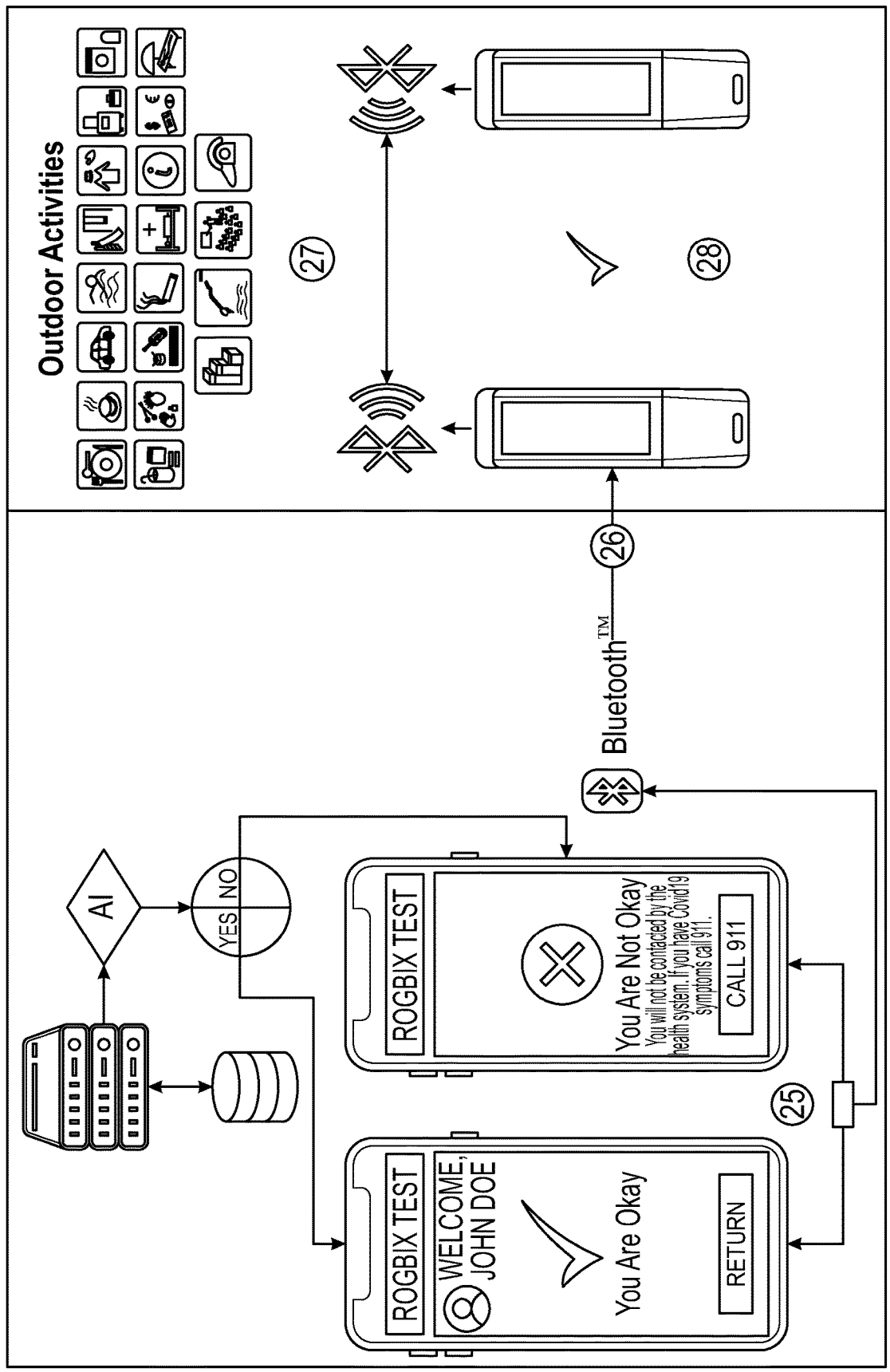
FIG. 4 is a flow diagram view of the association between devices, using the software application, to automatically communicate negative or positive test results from a tested disease condition according to the invention.
Figure 5:
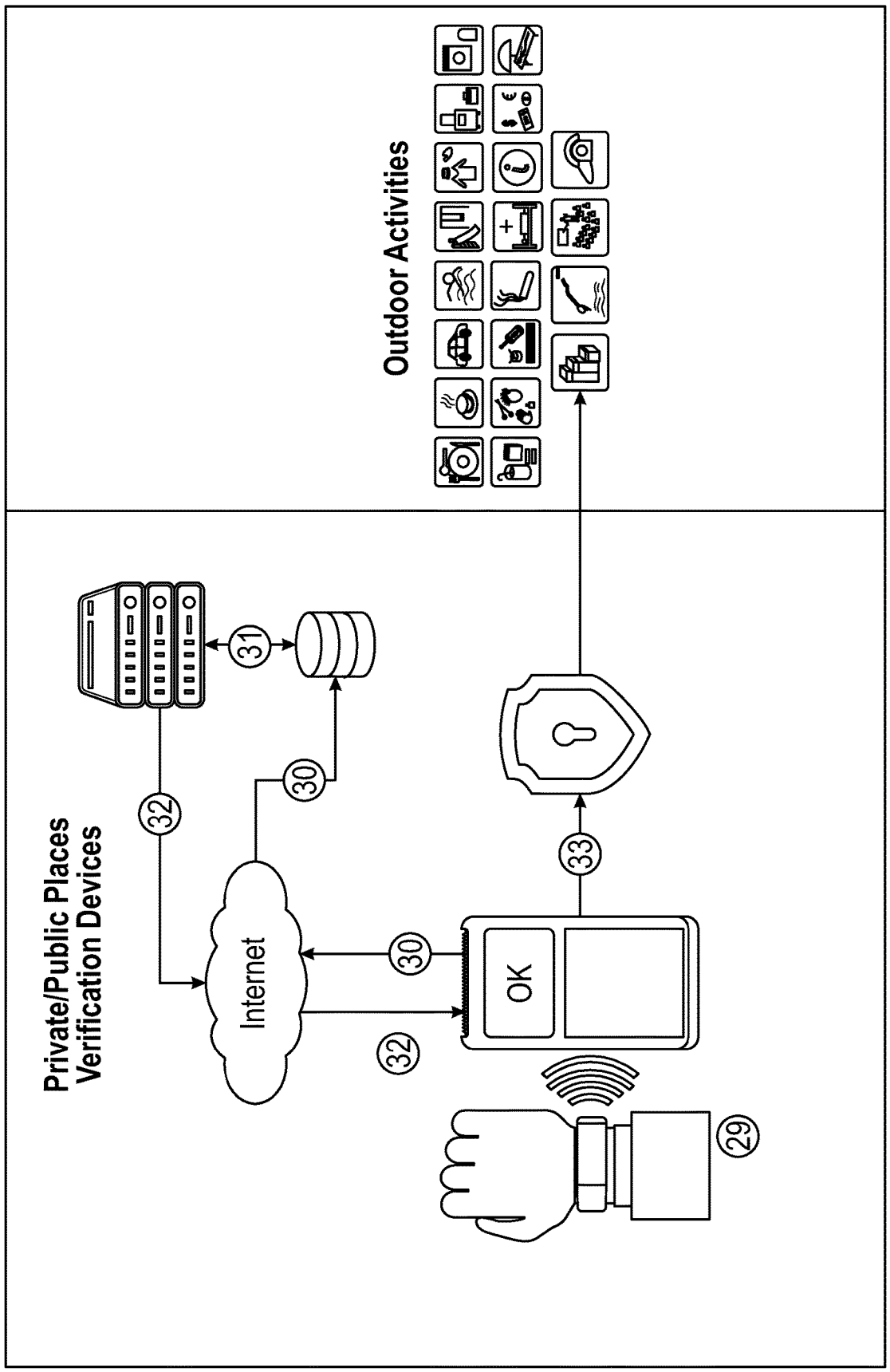
FIG. 5 is a flow diagram view of the association between devices, using the software application, to automatically communicate verification of negative or positive test results from a tested disease condition between user devices according to the invention.
Figure 6:
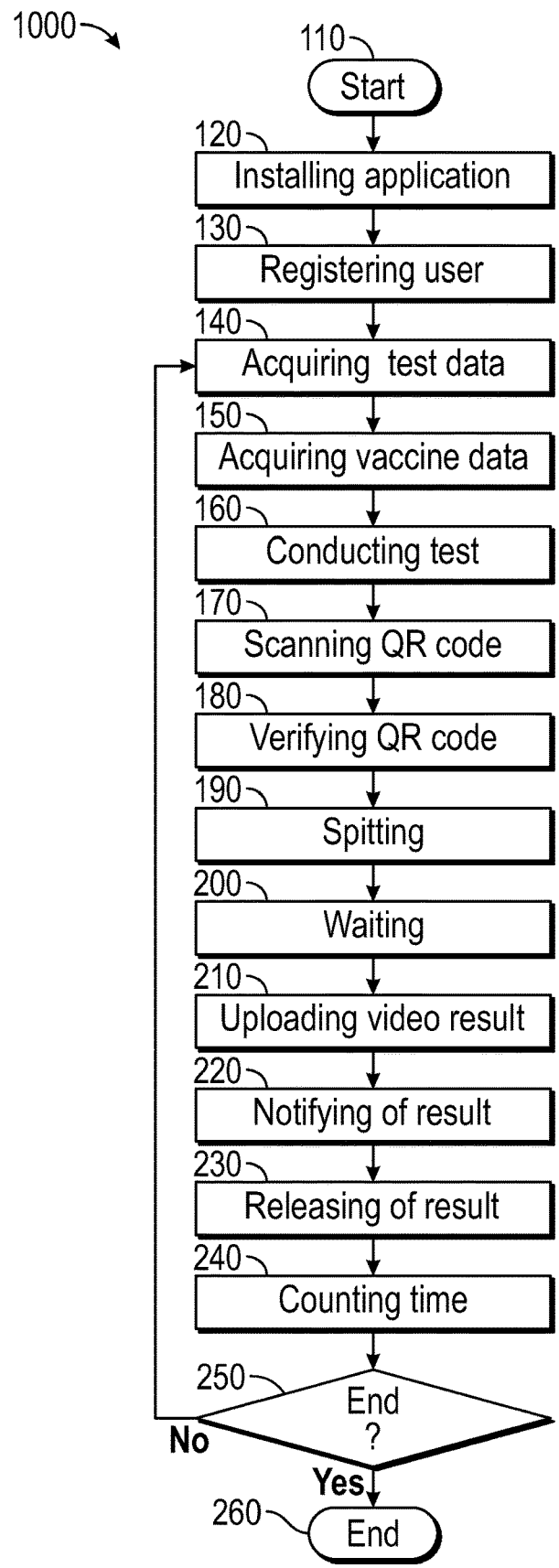
FIG. 6 is a flowchart view of sequence of steps used in the software application to remind a user to retest as a prior test expires and automatically communicate verification of negative or positive test results from a tested disease condition between user devices according to the invention.

The disease condition test state, positive or negative Covid infection state, information is emitted through light or vibration of a wearable device or personal smart device or phone as shown in FIGS. 4 and 5 and therein communicated to other users via the software application of the present invention. The invention functions with battery and works via the software application to communicate results electronically, spontaneously, simultaneously, quickly, and universally. It is non-invasive of personal privacy, does not prevent freedom of movement, is reliable, easy to use, and affordable. It is also autonomous and independent from any authority, individual/agent, or verification device. The user owns the device and decides when and where to use it. The device can be set in a vibration mode, light emitting mode, or both modes together.

The system is independent and is not connected to any public or private health system, nor does it report to any person or entity apart from the user. It exclusively transmits and informs a Covid Negative status among the users in a snapshot visual perception with no record or tracking.

In case that the saliva test results Covid-positive, the platform of the present invention will only give this test result to the user so that he can seek medical help and take appropriate measures.

The present invention only functions among individuals who are identified as covid negative. It could also function with electronic devices which are adapted and integrated to the system, which could be placed at the entrance of buildings, venues, or anywhere where large gatherings take place, such as malls, cruise ships, churches, schools, stadiums, metros, airports, and other places of high agglomeration or simultaneous confluence of people.

The system informs the covid free condition of the user in real time (RT) through the emission of an intermittent green light, visible to the naked eye, which is emitted by a user's wearable device (bracelet, smartwatch, brooch, button, or necklace.) The emission of the green light indicates that at the moment of flash emissions the user is covid negative.

The algorithm function authorizes the emission of the light by the user and it is transmitted from a ROGBIX system's server platform, where a database and index are kept. It does not include names of persons but only codes and numbers. The system transmits to the device, in real time, the negative result of the saliva antigen test of each user. The validity of each test result lasts five days and the transmission of light is good only during that time. Once this period ends the light goes off until the user takes another self-saliva test and gets a negative result.

The invention can be made available to non-profit organizations or can be exploited commercially at modest costs. Although the saliva test used as a part of the present invention has to be taken constantly (every 6 days), it is very affordable, as is the platform, so that it can be economically available to everyone on the planet.

The present invention may include a wearable device, such as any smart-device running the software application of the present invention, which, using the software of the present invention, makes possible the quick identification of Covid infection negative status among known individuals, as well as with strangers, who are also wearing the device. This technological invention communicates a covid free status among users without personal scrutiny or review, allowing them to meet without observing social distancing, without masks and without having to present any kind of verification, documentation, or the cellphones proofs, or any other proof, to a verifier agent or to any other party.

This invention is for the users to reactivate their social interaction with health safety; thus, encouraging reactivation of social and economic activities. The system of the present invention communicates the user's covid free status through emission of light signals obvious to visual perception when users are in a proximity of 5 to 8 meters. Therefore, the present invention eliminates the necessity of scrutiny or verification since the covid free status is evident. Social distancing becomes unnecessary among individuals with a covid negative health status electronically transmitted in real time, and mutually shared by pairing technology.

The covid negative status is determined by the algorithm, which activates the communication upon a periodic and constant saliva antigen test, (every 6 days), to detect the covid 19 virus. The system has a pre-established methodology of electronic transmission for the taking of the test by the user and for the result to be transmitted to the system database. This uses face recognition, QR identifier codes, and other means to minimize the possibility of impersonation or falsehood.

Once the user transmits their data to a ROGBIX database (on an internet connected server for example), the program processes it through Artificial Intelligence (AI) and other mechanisms and application lies an algorithm formula to establish the covid free status. The system subsequently activates another algorithm, whose function is to send an order to the application for it to activate the signal, which produces the emission of the constant green light. This application transmits the command to the user's smartphone and from there to his sensorial handle or wearable device to display a colored light signal panel and vibration.

A sensorial device, as in the present invention, is worn by the user to receive and perform the command for transmitting the green light. The emitted green light communicates to others, who are pairing multiple users' wearable devices, that this user has a covid negative status. It is a cybernetic device to inter-communicate a covid negative status among its users. It has a computer configuration for the devices that can be worn to maximize an automatic/specific communication among individuals with equal covid negative status. The function is controlled by a computerized logarithmic program, which is activated once the user has complied with the control protocols, so that he can wear it as an inter-communication element characterized as a cyberhealth anti covid-19 person.

The ROGBIX' System is designed to register, through an application, the process of collection and test result of a sample of saliva for antigen saliva Covid-19 detection test. This is a self-administered test which is analyzed by the artificial intelligence (AI) and other means of the invented device to validate the collection of the sample, the identity of the sample donor, and his Covid 19 Negative test result.

The saliva test is non-invasive and can be taken by the individual himself just by following the easy methodology indicated. It makes the users' verification of a covid-free status fast and inexpensive.

The present invention uses facial recognition and the reading of the QR code printed or adhered to the test's box and to the test's components to verify the identity of the user and the authenticity of the test and the test result. The software application of the present invention identifies the date, hour, user's name, and smartphone number. Once the QR code is activated by reading it with the cellphone QR code reading software; and the recognition of the user is done (refer to FIG. 3), the system allows the smart phone access to video-transmission of microfilm to verify in real time the face recognition and the sealed box that contains the test components. The user's identity and the taking of the saliva sample are filmed in real time when the user spits out his saliva in the container that comes in the box and is then identified with the same QR code printed in the test's sealed box thereby creating a self-verifiable test and test result potential.

The system of the present invention allows the smart phone to film the pouring of the saliva sample on the test strip that comes in the box, which contains the reagent solution. This strip also has imprinted the same QR code as the box. The box has the following components: one saliva container; one swab and several test strips. Each component has the same QR code as the box.

The saliva sample is poured on the test strip containing the reagent. The reading of the QR code on this strip will be done by AI once a photograph of the result is taken and sent electronically to an internet server-based platform by the user's Smartphone, thus eliminating the possibility of impersonation of the user and the false representation of the test sample. Once the test is finished, the user takes a photograph of the test strip showing the QR code and the resulting color of the saliva and reagent mix. The photograph taken with his smartphone will be sent to a server platform running the software of the present invention to be analyzed by AI and other software means to determine the test result and confirm that such test corresponds to the same user who spat out the sample. When the reaction of the mixture of saliva and reagent is identified by the AI or other software the test result is determined. Once the negative result and the above-mentioned factors are verified, the platform is activated for this particular user who is then incorporated into the automatic self-identification system.

The user incorporation into the system activates his communication with other users of the present invention by pairing them through a wireless communication frequency so they can automatically inform each other of their Covid Free status. The mutual identification of the users and their Covid-Negative status will be made evident by an intermittent green light which is visible to others from a reasonable distance. This light is transmitted from the platform to an electronic device worn by the user. This device called CyberGath allows the user to meet with other equals (gather) without social distancing, without masks and with the certainty of non-contagion among themselves. This incorporation to the system application ends when the covid negative result of the self-application test is transmitted from the platform to the user's smartphone and from there to the wearable device in real time.

Once the user is activated in the platform the activation will be good for five days. Once these five days expire the transmission will automatically cease and the device will not operate until it is reactivated when the user takes a new saliva test and continues getting a covid negative test result.

In case of a positive test result the transmission will not be activated. However, the user will receive a signal from the platform indicating that the user should isolate and contact a health provider immediately. The software of the present invention will only disclose this information to the user. Once the user is medically discharged as a Covid patient, the user will be able to take another test in the system, and when his result shows covid 19 negative he might be incorporated into the system and his covid free status transmission to his CyberGath may start again. The figures included with this document visually explain how the systems, application, and device work.

As shown in FIG. 1 the following is how an individual can become a user of the present invention as one example.

The user downloads the application to a smartphone or other device and a registration application appears on the screen. After the user fills the required registration information, they send it to a private database, as in the present invention, where it is registered. This database is not available to third parties.

When the information is registered in the database, the server creates an account for the user's smartphone and sends a request to the application running the user's device to identify the user's smartphone number.

After the smartphone is identified the information is sent to the server which in turn registers the information and the telephone number in the database.

The server generates a code and sends it to the server of the SMS service provider, requesting that the provider re-sends such code to the user.

The provider of service sends the SMS to the user with the assigned code. The provider of the service confirms the sending of the SMS to the ROGBIX server.

The new user inputs the code number sent to him by the server of the SMS service provider and re-sends it to the server by pressing the button titled "CONFIRMED."

The server confirms the code number and immediately gives the user access to the ROGBIX digital self-identification service. Only press "START TEST"

Figure 2:
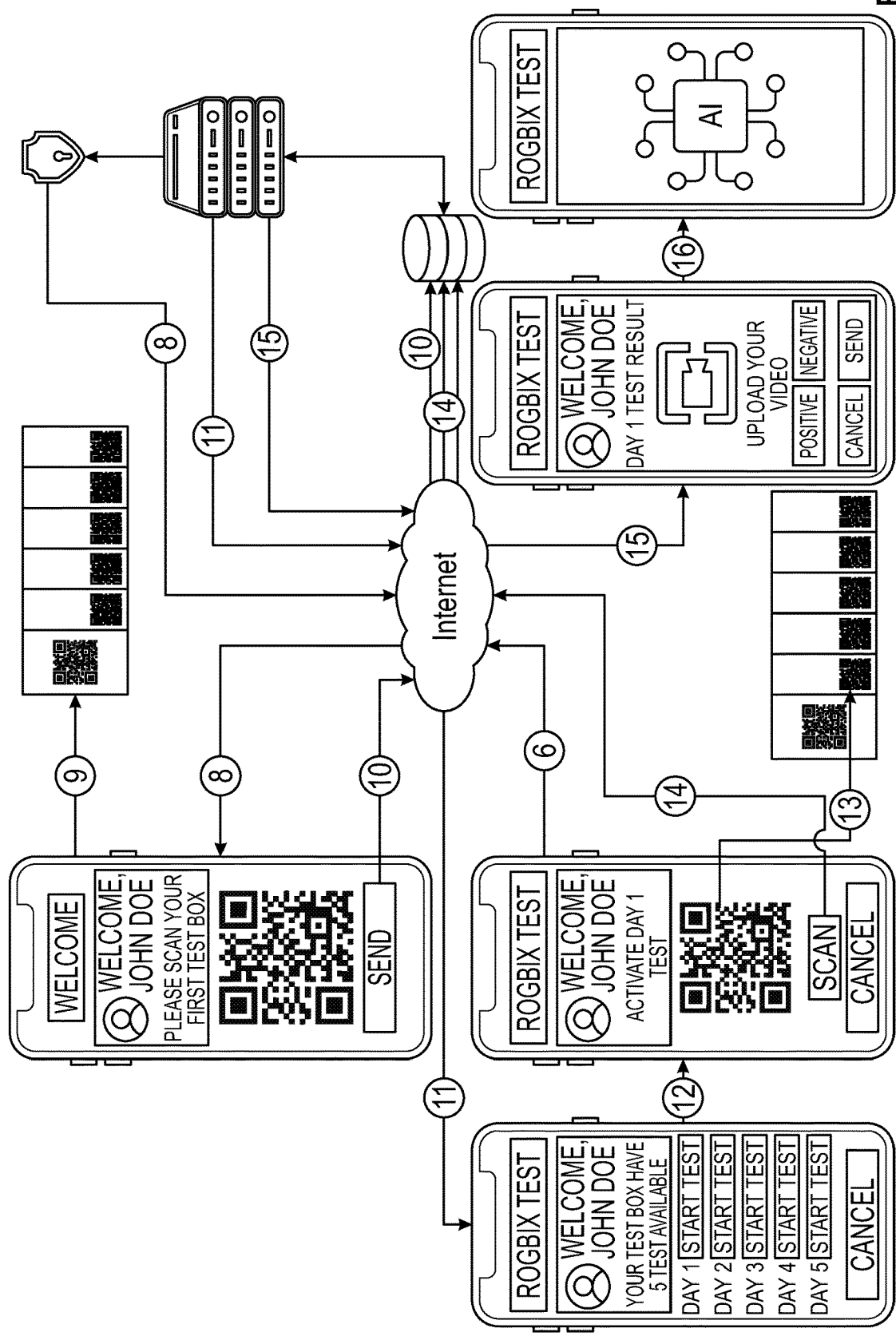
FIG. 2 is a flow diagram view showing the initiation of a test for a disease condition (such as testing for Covid positive or negative infection status) according to the invention.

As shown in FIG. 2 activation for test taking proceeds with the following steps as one example.

The server sends a welcome screen to the user's smartphone and requests that he registers his first box of saliva antigen test for Covid-19 detection.

To do that, the software application of the present invention opens a camera for the scanning of the QR Code that application ears in an insert inside the box containing the antigen test of this user. It is not allowed to share a test of the same box with anybody else.

The QR code is verified with the database to confirm that the same has not been used before and to assign it to the user of the smartphone that scanned it.

After the database confirms that the QR code corresponding to the test box has not been used before, it is registered on behalf of the user. The server opens a screen in the user's smartphone identifying all available tests inside the box. The individual tests available in the box have the same QR code attached.

The screen that opens in the smartphone indicates the tests inside the box, and the option the user has to initiate the process of taking each one of the tests on the day he deems necessary. This is done by activating them by touching the respective buttons corresponding to each one of the tests, labeled "START TEST".

In the smartphone screen, the test immediately available is green. Tests not yet used are matte gray. Those which have already been used are black and will not be able to be re-activated.

For health safety the international scientific community agrees on the validity of the test report for no more than four days counted from the 24th hour following the time the test was taken. In accordance, the present invention deactivates the electronic identification of a user that has not renewed his saliva test report by taking a new test on the sixth day after the last test was taken.

For the safety of its users the system of the present invention has a program driven by an algorithm whose variables are based upon the number of days in which a possible onset of symptoms may occur or the standard period of time in which a transmissible asymptomatic viral load incubation may occur according with the counts average established by the scientific community.

Once the first test is done, as it's cycle ends the system sends a notification to the user's smartphone asking him for a new test report within 24 hours; otherwise the electronic self-information system stops transmitting to the user and the green light and transmission from platform turns off for this device.

If the user takes a new test and the test shows a Covid 19 Negative result, the self-information system of the user is re-activated. The User presses the button that corresponds to the available test on the screen (TEST 1; or TEST 2; or TEST 3; or TEST 4; or TEST 5) and that button opens up the test screen. This screen requests permission to open the smartphone back camera to scan the QR code of the test corresponding to the sample of saliva to be analyzed.

Figure 3:
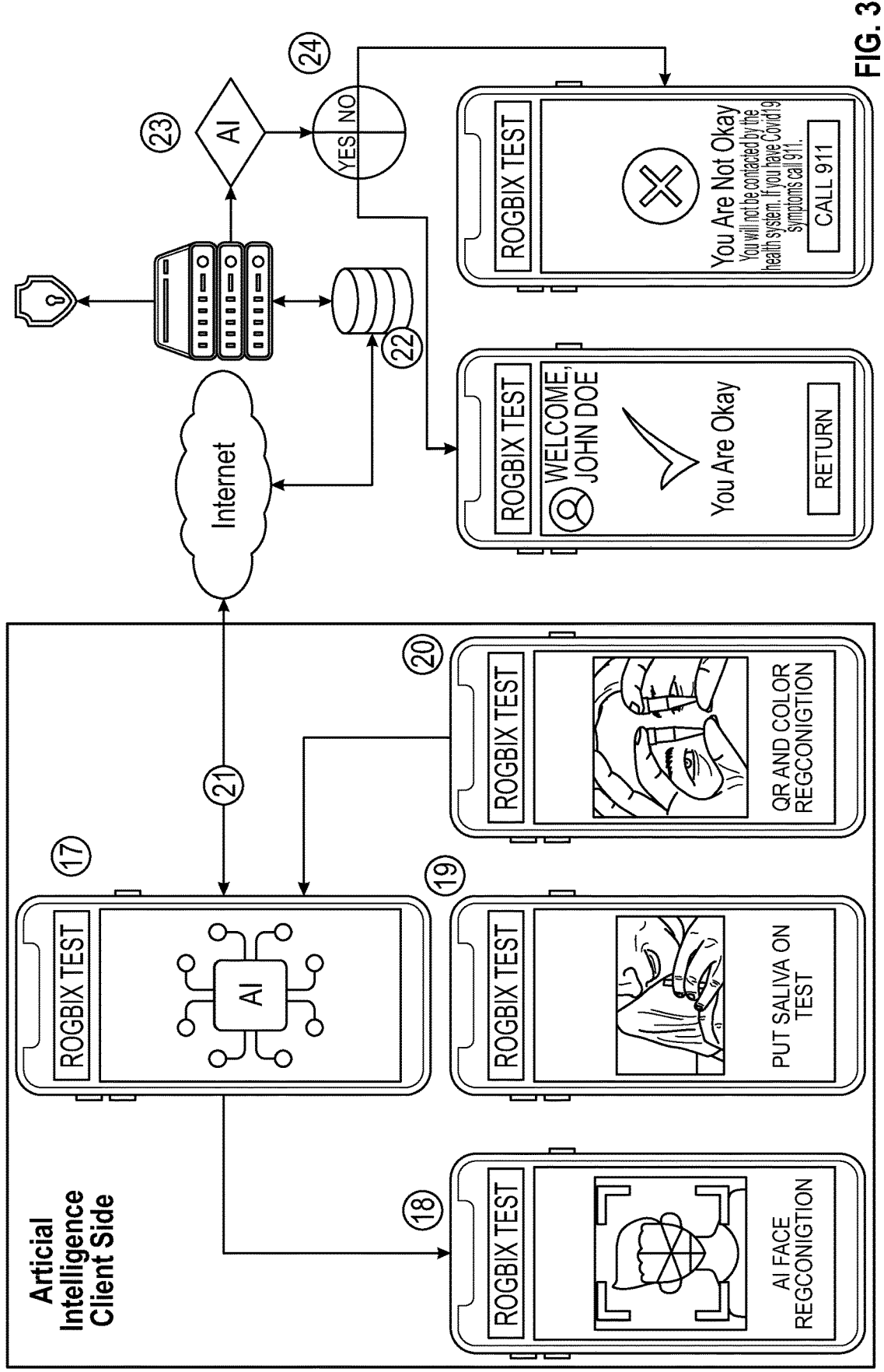
FIG. 3 is a flow diagram view showing the implementation and additions of a verifiable test for a disease condition (such as testing for Covid infection status) according to the invention.

The user must scan the QR code. When the button "SEND SCAN" is pressed, the "send function" of the QR code is activated and the server validates the QR code in the database. Once the database confirms that the test is available and has not been used before; the server sends the order to the application to open up the screen that allows the user to film the video when he collects his own saliva sample as well as when he pours it on the test strip to be mixed with the reagent. When the video icon is press this activates the AI in the system As shown in FIG. 3, Artificial Intelligence procedure. When the AI of the present invention is activated, it requests the facial recognition of the user, unless the user had registered a previous facial recognition. If he does not have a previous recognition, the system will request the user to register his face before it can continue. To comply with the Face Recognition requirement, the front camera of the user's smartphone opens up to proceed with the face identification. The camera opens up in order for the user to film the collection of the saliva as he spits it out in the container that has been placed, displaying its QR Code, in front of the camera.

The entire process of collecting the sample is carried out in the user's private sphere and he can easily do it with his personal smartphone. Fifteen to twenty minutes after the saliva is placed in the test strip to be mixed with the reagents the result of the test is evidenced by a change in the color of the test strip sample.

After 15 to 20 minutes the user can upload a photograph showing the QR code of the test strip where the saliva was poured. This action (upload photograph) allows the AI of the present invention to recognize the result of the Covid 19 test. If the user decides to send the test strip result, after the previous information is uploaded in the database, this information is processed by the server. The server transmits the result by emitting a constant digital transmission of the result, exclusively addressed to the user's smartphone; and from it to the wearable device that the user has chosen to wear for showing the green light indicator of his covid negative condition, which is updated in real time. The user's information is registered in the database and will not be shared with any third party. The server processes the information of the results received from the user's smartphone to identify, through Artificial Intelligence (AI), the pairing between the user's identity, his smartphone number, the test QR code, and the video of the collection of the sample taken for Face Recognition. All these elements must correspond to the same user.

The algorithm of the present invention (the program) makes a calculation based on the data received and sends the result to the user's smartphone. The program activates an electronic notification of the test result to be sent to the user's smartphone during five consecutive days. After this period (5 days) the electronic notification stops; unless a new saliva test is transmitted from the user's smartphone to the platform complying with the identification protocols.

As shown in FIG. 4. Device synchronization method for the covid-free self-identification. If the result of the test is Covid 19 positive, the user receives this information sent by the server exclusively to the user's smartphone. The system will be suspended for this user until he undergoes a new PCR-Negative test in a laboratory previously identified by the platform. In the future the user will be able to join the system with a negative saliva antigen test again.

If the result of the test is Covid 19 negative, the notification of this result will be digitally sent by the server exclusively to the user's smartphone. The user, upon receiving the digital notification, is able to activate his smartwatch or smart bracelet incorporating it to the system and ready to inter-connect (through pairing via Bluetooth), with other devices operating the present invention in close proximity. Once interconnected the devices communicate among themselves the same covid-free condition of the users, overcoming the social distancing among peers or equals.

The smartphone communicates the updated information to the user's smartwatch, which is synchronized with his smartphone. The test result contained therein, received from the platform shared with the smartwatch or bracelet through Bluetooth technology. The smart watch/bracelet in turn communicates with other devices through pairing for the voluntary and automatic interchange among the users of the information that they are covid free individuals. The covid-free identity status is voluntarily communicated by the user through green intermittent light, visible to the naked eye. This activates the function "Identified-Application Approach" to auto-identify that user of a bracelet (such as the ROGBIX bracelet with tab device as shown in FIG. 4, element 28, in close proximity share a similar covid negative status.

Enabling the activation of a vibration when the user's smart device is within ten meters of a second user having a negative test result feature has multiple available programming solutions that are already well known in the art. For example, one readily available programming solution a computer programmer might use to enable the proximity trigger is the following: in order to implement the proximity trigger to activate a vibration when the user's smart device is within 10 meters of a second user having a negative test result, a global grid of connected areas can be used to sort the users into potential for proximity to each other minimizing processing by limiting the number of other users that need to be compared to each other because only users within a given grid are compared to each other by location coordinates. When the distance between user coordinates is the ten meter distance or less, the device is triggered to enable an alert and trigger the vibration feature of the device it is operating on. Users at the edges of the grids within ten meters of another grid's border are compared to users in the adjacent grid that are also close to that border.

As shown in FIG. 5. Safe Social Gathering and Economic Recovery. In places where people gather such as: workplaces, churches, schools, universities, airports, malls, cruise ships, and similar; the platform of the present invention can be used as an application location which can be installed in such places, as long as they have or acquire a radio frequency identifier or automatic identifier or reading devices placed in the entrances. The automatic identifier currently requires a base operating IOS system or an Android 8 or higher but can be upgraded and altered as technology and operating systems change over time.

The application of the present invention is able to read all the wearable electronic devices communicating with the system to identify a Covid Free status of the user. These readers or automatic identifiers are able to receive, from the platform, instant and updated information of the Covid-Free saliva test results taken by users within the five previous days. At the same time, the automatic identifier is able to obtain, at the discretion of the user, the information concerning the double vaccination of the user. This information may be revealed to the automatic identifier through two check marks that can be emitted by the device: One in the color green for the covid negative identification; and another one in the color blue to identify the double vaccination received by the user.

For the double vaccination identification the present invention maintains a simple special procedure of verification, additional to the system of covid free status identification. The reading device or automatic identifier sends the code read in the smart watch equipped with wireless communications technology which integrates the automatic identifier (such as a radio frequency identifier) function to the server. The server receives the information request, compares it, and makes a logical decision (through an algorithm). The server sends its answer to a reading device or automatic identifier. The premise or venue grants access to individuals who are identified, through the CyberGath device, as vaccinated and covid free status, so that they can improve health safety in their place or compound.

By knowing their mutual covid free status, people who are wearing CyberGath can integrate in clusters in which the transmission rate may drop to zero since all CyberGath users who interact have no risk of contagion. The system of matching CyberGath users by wireless pairing technology leads to organizations such as schools, churches, arm forces, and first responders, etc. to establish themselves as covid free clusters in which social coexistence is normalized. Their members spontaneously identify each other by a cybernetic means that lets them instantly know that there is no possibility of contagion among users. The system allows that even strangers who wear the CyberGath can overcome the barriers of distancing by matching with the devices of other users with the same covid negative status. Consequently, the clusters can integrate newcomers, expanding infinitely as long as they are cyber identified as Covid Free. As more people join covid free clusters, the CyberGath community expands bringing life to normal.

The advantage of using the CyberGath does not exclude the caution and measurements that its users must take when they are in proximity to persons who are not identified as Covid negative. In these cases, social distancing measures shall be kept. The expansion of these clusters of CyberGath users brings the reactivation of the economy that has been affected by the restraint of interaction because of the danger of contagion. In industries or activities such as tourism, cruise ships, airports, churches and similar crowded venues, the spontaneous cyber-identification of the persons as covid negative improves the activities.

The device makes possible the gathering of people by bringing certainty about the covid-negative status. The generalize use of the CyberGath system will reduce the spread of coronavirus, since to the extent that communities are integrated into this system forming Clusters of Covid free users where the virus does not exist, and therefore disappears, since its members do not have the capacity to infect or be infected among themselves, so the absence of the virus in these groups cancels the possibility of replication and survival of Covid-19. Consequently, the CyberGath elements of the present inventions systems offer a way to restore social interaction and therefore economic reactivation with health safety. It is at the same time a means to avoid the replication of the virus causing its eventual eradication; thus restoring normal life in the planet.

In a preferred embodiment of the invention, there is a method for a user to self-identify a tested condition status and to actively communicate said tested condition status to a second user comprising installing an application on a first smart device having screen; registering said user; acquiring a test data for a condition, if available, from an authorized test data reporter; conducting a test on said user for said condition; comprising scanning a visual code; verifying said visual code; collecting a bodily fluid sample from said user; testing said bodily fluid, verifying test results; generating a new test result having a positive or negative result for a condition and creating a notice in a window on said smart device comprising a first visible solid color panel display (VSCPD) covering more than fifty percent of said screen when said new test result is negative for a tested condition and no VSCPD when said new test result is positive.

In an embodiment of the invention, there is a method wherein said notice further comprises a first countdown timer for a negative result for a condition wherein said notice further comprises removing said first VSCPD after expiration of said first countdown timer and said method further comprises returning to the conducting a test step and continues.

In an embodiment of the invention, there is a method wherein said conducting a test step further comprises obtaining a permission from said user to release said test result.

In an embodiment of the invention, there is a method wherein said first VSCPD is green for indicating when said new test result is a negative result.

In an embodiment of the invention, there is a method wherein said visual code is comprised of a QR code.

In an embodiment of the invention, there is a method wherein said notice further comprises a vibration of said first smart device when it is within ten meters of a second user using a device as in the present invention having a negative test result.

In an embodiment of the invention, there is a method wherein said test data further comprises a vaccine status data having a positive and a negative vaccination status for vaccination against said condition and said notice further comprises a second VSCPD covering more than fifty percent of said screen when said vaccine status data is positive for a vaccination against said condition and no second VSCPD when said vaccine status data is negative, wherein said first VSCPD and said second VSCPD alternate being displayed in said display window.

In an embodiment of the invention, there is a method wherein said notice further comprises a second countdown timer for a positive vaccination status wherein said notice further comprises removing said second VSCPD after expiration of said second countdown timer and said method further comprises returning to the conducting a test step and continues.

In an embodiment of the invention, there is a method wherein said second VSCPD is blue for indicating when said vaccination status is a positive vaccination status.

In an embodiment of the invention, there is a method wherein said notice further comprises a vibration of said first smart device when it is within ten meters of a second user using a device as in the present invention having a negative test result.

In an embodiment of the invention, there is a method for a user to self-identify a tested covid condition status and to actively communicate notice of said tested condition status to a second user using this method, comprising installing an application on a smart-phone connected to a smart device having a screen; registering said user; acquiring a test data for said tested covid condition from an authorized test data reporter; conducting a test on said user for said condition; comprising scanning a visual code; verifying said visual code; collecting a saliva sample from said user; testing said saliva; verifying said test and producing a results code; generating a test result having a positive or negative result for said tested covid condition and creating a notice in a window on said smart device comprising a visible solid color panel display (VSCPD) covering more than fifty percent of said screen when said test result is negative for a tested covid condition and no VSCPD when said test result is positive.

In an embodiment of the invention, there is a method wherein said notice further comprises a countdown timer for a negative result of a covid condition wherein said notice further comprises removing said VSCPD after expiration of said countdown timer and said method further comprises returning to conducting a test step and continues.

In an embodiment of the invention, there is a method wherein said conducting a test step further comprises a selecting a voluntary activation of the smart device by said user to release said test result.

In an embodiment of the invention, there is a method wherein said VSCPD is green for indicating when said covid test result is negative.

In an embodiment of the invention, there is a method wherein said visual code is comprised of a QR code.

In an embodiment of the invention, there is a method wherein said notice further comprises a vibration or light mode activation of said smart device when it is within ten meters of a second user using the same method having a negative test result, causing an electronic pairing and activating said vibration or light mode lighting both devices.

In an embodiment of the invention, there is a method wherein said test data further comprises a vaccine status data having a positive and a negative vaccination status for vaccination against said condition and said notice further comprises a second VSCPD covering more than fifty percent of said screen when said vaccine status data is positive for a vaccination against said condition and no second VSCPD when said vaccine status data is negative wherein said first VSCPD and said second VSCPD alternate being displayed in said display window.

In an embodiment of the invention, there is a method wherein said notice further comprises a second countdown timer for a positive vaccination status wherein said notice further comprises removing said second VSCPD after expiration of said second countdown timer and said method further comprises returning to the conducting a test step and continues.

In an embodiment of the invention, there is a method wherein said second VSCPD is blue for indicating when said vaccination status is a positive vaccination status.

The invention has been described by way of examples only. Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the claims.

Although the invention has been explained in relation to various embodiments, it is to be understood that many other possible modifications and variations can be made without departing from the spirit and scope of the invention.

The invention claimed is:

1. A method for a user to self-identify a tested condition status and to actively communicate said tested condition status to a second user comprising
    installing an application on a first smart device having screen,
    registering said user,
    acquiring a test data for a condition if available from an authorized test data reporter,
    conducting a test on said user for said condition comprising,
        scanning a visual code,
        verifying said visual code,
        collecting a bodily fluid sample from said user,
        testing said bodily fluid,
        verifying test results,
        generating a new test result having a positive or negative result for a condition, and
    creating a notice in a window on said smart device comprising a first visible solid color panel display (VSCPD) covering more than fifty percent of said screen when said new test result is negative for a tested condition and no VSCPD when said new test result is positive wherein said notice further comprises a first countdown timer for a negative result for a condition wherein said notice further comprises removing said first VSCPD after expiration of said first countdown timer and said method further comprises returning to the conducting a test step and continues.

2. A method for a user to self-identify a tested condition status and to actively communicate said tested condition status to a second user comprising
    installing an application on a first smart device having screen,
    registering said user,
    acquiring a test data for a condition if available from an authorized test data reporter,
    conducting a test on said user for said condition comprising,
        scanning a visual code,
        verifying said visual code,
        collecting a bodily fluid sample from said user,
        testing said bodily fluid,
        verifying test results,
        generating a new test result having a positive or negative result for a condition, and
    creating a notice in a window on said smart device comprising a first visible solid color panel display (VSCPD) covering more than fifty percent of said screen when said new test result is negative for a tested condition and no VSCPD when said new test result is positive wherein said first VSCPD is green for indicating when said new test result is a negative result.

3. A method for a user to self-identify a tested condition status and to actively communicate said tested condition status to a second user comprising
    installing an application on a first smart device having screen,
    registering said user,
    acquiring a test data for a condition if available from an authorized test data reporter,
    conducting a test on said user for said condition comprising,
        scanning a visual code,
        verifying said visual code,
        collecting a bodily fluid sample from said user,
        testing said bodily fluid,
        verifying test results,
        generating a new test result having a positive or negative result for a condition, and
    creating a notice in a window on said smart device comprising a first visible solid color panel display (VSCPD) covering more than fifty percent of said screen when said new test result is negative for a tested condition and no VSCPD when said new test result is positive wherein said notice further comprises a vibration of said first smart device when it is within ten meters of a second user having a negative test result.

4. A method for a user to self-identify a tested condition status and to actively communicate said tested condition status to a second user comprising
    installing an application on a first smart device having screen,
    registering said user,
    acquiring a test data for a condition if available from an authorized test data reporter,
    conducting a test on said user for said condition comprising,
        scanning a visual code,
        verifying said visual code,
        collecting a bodily fluid sample from said user, testing said bodily fluid,
verifying test results,
generating a new test result having a positive or negative result for a condition, and
creating a notice in a window on said smart device comprising a first visible solid color panel display (VSCPD) covering more than fifty percent of said screen when said new test result is negative for a tested condition and no VSCPD when said new test result is positive wherein said test data further comprises a vaccine status data having a positive and a negative vaccination status for vaccination against said condition and said notice further comprises a second VSCPD covering more than fifty percent of said screen when said vaccine status data is positive for a vaccination against said condition and no second VSCPD when said vaccine status data is negative wherein said first VSCPD and said second VSCPD alternate being displayed in said display window.

5. The method of claim 4 wherein said notice further comprises a second countdown timer for a positive vaccination status wherein said notice further comprises removing said second VSCPD after expiration of said second countdown timer and said method further comprises returning to the conducting a test step and continues.

6. The method of claim 4 wherein said second VSCPD is blue for indicating when said vaccination status is a positive vaccination status.

7. A method for a user to self-identify a tested condition status and to actively communicate said tested condition status to a second user comprising
installing an application on a first smart device having screen,
registering said user,
acquiring a test data for a condition if available from an authorized test data reporter,
conducting a test on said user for said condition comprising,
scanning a visual code,
verifying said visual code,
collecting a bodily fluid sample from said user,
testing said bodily fluid,
verifying test results,
generating a new test result having a positive or negative result for a condition, and
creating a notice in a window on said smart device comprising a first visible solid color panel display (VSCPD) covering more than fifty percent of said screen when said new test result is negative for a tested condition and no VSCPD when said new test result is positive wherein said notice further comprises a vibration of said first smart device when it is within ten meters of a second user having a negative test result.

8. A method for a user to self-identify a tested covid condition status and to actively communicate notice of said tested condition status to a second user using this method comprising
installing an application on a smart-phone connected to a smart device having a screen,
registering said user,
acquiring a test data for said tested covid condition from an authorized test data reporter,
conducting a test on said user for said condition comprising,
scanning a visual code,
verifying said visual code,
collecting a saliva sample from said user,
testing said saliva,
verifying said test and producing a results code,
generating a test result having a positive or negative result for said tested covid condition, and
creating a notice in a window on said smart device comprising a visible solid color panel display (VSCPD) covering more than fifty percent of said screen when said test result is negative for a tested covid condition and no VSCPD when said test result is positive wherein said notice further comprises a countdown timer for a negative result of a covid condition wherein said notice further comprises removing said VSCPD after expiration of said countdown timer and said method further comprises returning to conducting a test step and continues.

9. A method for a user to self-identify a tested covid condition status and to actively communicate notice of said tested condition status to a second user using this method comprising
installing an application on a smart-phone connected to a smart device having a screen,
registering said user,
acquiring a test data for said tested covid condition from an authorized test data reporter,
conducting a test on said user for said condition comprising,
scanning a visual code,
verifying said visual code,
collecting a saliva sample from said user,
testing said saliva,
verifying said test and producing a results code,
generating a test result having a positive or negative result for said tested covid condition, and
creating a notice in a window on said smart device comprising a visible solid color panel display (VSCPD) covering more than fifty percent of said screen when said test result is negative for a tested covid condition and no VSCPD when said test result is positive wherein said VSCPD is green for indicating when said covid test result is negative.

10. A method for a user to self-identify a tested covid condition status and to actively communicate notice of said tested condition status to a second user using this method comprising
installing an application on a smart-phone connected to a smart device having a screen,
registering said user,
acquiring a test data for said tested covid condition from an authorized test data reporter,
conducting a test on said user for said condition comprising,
scanning a visual code,
verifying said visual code,
collecting a saliva sample from said user,
testing said saliva,
verifying said test and producing a results code,
generating a test result having a positive or negative result for said tested covid condition, and
creating a notice in a window on said smart device comprising a visible solid color panel display (VSCPD) covering more than fifty percent of said screen when said test result is negative for a tested covid condition and no VSCPD when said test result is positive wherein said notice further comprises a vibration or light mode activation of said smart device when it is within ten meters of a second user having a negative test result, causing an electronic pairing, and activating said vibration or light mode lighting both devices.

11. A method for a user to self-identify a tested covid condition status and to actively communicate notice of said tested condition status to a second user using this method comprising
- installing an application on a smart-phone connected to a smart device having a screen,
- registering said user,
- acquiring a test data for said tested covid condition from an authorized test data reporter,
- conducting a test on said user for said condition comprising,
  - scanning a visual code,
  - verifying said visual code,
  - collecting a saliva sample from said user,
  - testing said saliva,
  - verifying said test and producing a results code,
  - generating a test result having a positive or negative result for said tested covid condition, and
- creating a notice in a window on said smart device comprising a visible solid color panel display (VSCPD) covering more than fifty percent of said screen when said test result is negative for a tested covid condition and no VSCPD when said test result is positive wherein said test data further comprises a vaccine status data having a positive and a negative vaccination status for vaccination against said condition and said notice further comprises a second VSCPD covering more than fifty percent of said screen when said vaccine status data is positive for a vaccination against said condition and no second VSCPD when said vaccine status data is negative wherein said first VSCPD and said second VSCPD alternate being displayed in said display window.

12. The method of claim 11 wherein said notice further comprises a second countdown timer for a positive vaccination status wherein said notice further comprises removing said second VSCPD after expiration of said second countdown timer and said method further comprises returning to the conducting a test step and continues.

13. The method of claim 11 wherein said second VSCPD is blue for indicating when said vaccination status is a positive vaccination status.

\* \* \* \* \*